(12) United States Patent
Ghione et al.

(10) Patent No.: US 6,231,855 B1
(45) Date of Patent: May 15, 2001

(54) MONOCLONAL ANTIBODIES AS ANTIDOTES FOR ANTHRACYCLINE ANTIBIOTICS

(75) Inventors: Mario Ghione; Andrea Balsari; Maria Ines Colnaghi, all of Milan (IT)

(73) Assignee: Istituto Nazionale per lo Studio e la Cura Dei Tumori, Milan (IT)

( * ) Notice: Subject to any disclaimer, the term of this patent is extended or adjusted under 35 U.S.C. 154(b) by 0 days.

(21) Appl. No.: 08/056,382

(22) Filed: May 4, 1993

Related U.S. Application Data

(63) Continuation-in-part of application No. 07/848,753, filed on Mar. 10, 1992, now abandoned.

(30) Foreign Application Priority Data

Mar. 12, 1991 (IT) .............................. MI91A0660

(51) Int. Cl.$^7$ ...................... A61K 39/395; C07K 16/00; C12P 21/08
(52) U.S. Cl. ................... 424/130.1; 424/156.1; 530/388.1; 530/388.9
(58) Field of Search ............... 424/85.8, 130.1, 424/156.1; 530/388.1, 388.9, 389.8; 435/240.27

(56) References Cited

U.S. PATENT DOCUMENTS 5,177,016 * 1/1993 Balsari et al. .................. 435/240.27

OTHER PUBLICATIONS

R.K. Scopes "Protein Purification" Springer–Verlag, New York, 1982 p. 16.*

J.F. Robyt et al. "Biochemical Techniques—Theory and Practice" Brools/Cole Pub. Co., Monterey, 1987. pp. 263–264.*

R.F. Boyer, "Modern Experimental Biochemistry", Addison–Wesley Pub. Co., Reading MA, 1986 pp. 44–46.*

E. Harlow et al. "Antibodies—A Laboratory Manual" Cold Spring Harbor, NY 1988 p. 287.*

IB Sneddon et al "Practical Dermatology" 4$^{th}$ Ed. E. Arnold, London 1983 pp. 193–199.*

A. Balsari et al. Anticancer Res 10:129 1990.*

A. Balsari et al. Int. J. Cancer 42:798 1988.*

A. Balsari et al Int J. Cancer 47:889 1991.*

* cited by examiner

*Primary Examiner*—Lorraine Spector
(74) *Attorney, Agent, or Firm*—Birch, Stewart, Kolasch & Birch, LLP

(57) ABSTRACT

Anti-anthracycline antibiotic monoclonal antibodies are useful as antidotes of the anthracycline antibiotics themselves, as well as for the treatment of anthracycline extravasation lesions and alopecia.

15 Claims, No Drawings

MONOCLONAL ANTIBODIES AS ANTIDOTES FOR ANTHRACYCLINE ANTIBIOTICS

This is a continuation-in-part of application Ser. No. 07/848,753, now abandoned filed on Mar. 10, 1992.

The present invention relates to anti-anthracycline antibiotic monoclonal antibodies (MAb) as antidotes for said drugs.

BACKGROUND OF THE INVENTION

Anthracycline antibiotics are a widely investigated class of compounds having antitumor activity. Particularly, doxorubicin (DXR) has been used for a long time in antitumor chemotherapy protocols.

The clinical usefulness of anthracycline antibiotics is limited by serious side effects such as cardiomyopathy, bone-marrow depression, gastrointestinal tract mucositis and, if there is drug leakage at the injection site, local tissue necrosis.

Particularly, local side effects are represented by sloughing ulcerations and occur when the drug is inadvertently extravasated during administration or oozes out through compromised vein walls. Damage from extravasation is not immediately apparent, but comes out days later and slowly progresses to involve superficial and deep structures, such as soft tissues and nerves and tendons as well. The severe course of this type of lesions, which can be experimentally reproduced in animal models (see Balsari A., et al, Chemotherapy 5: 324–329, 1989), is due to the long term persistence of residual active drug at the extravasation sites.

Another peculiar side effect consists in alopecia, which is due to the inhibiting activity exerted by anthracyclines on the continuously growing cells of hair roots. Alopecia occurs in almost the totality of the patients treated with anthracycline drug. Such effect is not life endangering per se, but severely harasses the patient and deteriorates the quality of life.

Many attempts have been made to reduce the toxicity of anthracycline antibiotics, while retaining substantially unaffected the antitumor activity thereof. For this purpose, two main approaches have been taken: (a) synthesis of DXR analogues and derivatives; and (b) combination with substances which are thought likely to interfere with factors claimed to be responsible for the toxic effects of these drugs, such as vitamin E, ubiquinone, chelating agents and the like.

However, no efficient method of treatment has been so far described for the above-mentioned highly distressing tissue lesions. In a number of cases surgical intervention is considered for wide removal of the lesions in the attempt of salvaging structures and retain function. In some cases, limb amputation and/or skin grafting may be necessary. Local infiltration at extravasation sites with sodium bicarbonate or hyaluronidase or saline solution is of limited usefulness, if any.

Many approaches have been suggested to reduce alopecia incidence and extent by decreasing the scalp blood flow with the use of tourniquets, tight refrigerated caps, etc.

So far, the above-described problems have not satisfactorily been solved.

BRIEF SUMMARY OF THE INVENTION

Now it has surprisingly been found the MAbs anti-anthracycline can reduce the toxicity of these drugs, while substantially retaining the antitumor efficacy. In fact, a higher detoxifying affect of monoclonal antibodies in normal cells or tissues than in tumor cells or tissues has been evidenced from both in vitro and in vivo tests. This is particularly surprising in that previous reports on the detoxifying activity of anti-drug MAbs, such as those against digoxin (Hunter, et al, J. Immunol., 129, 1165–1172, 1982) evidenced no tissue or organ specificity. In those cases, detoxication has been assigned to an inactivation of the drug.

Previous research on anti-DXR polyclonal antibodies (Chien, et al, Immunochemistry, 12, 291–296 1975; Savaray, et al, Res. Comm. Chem. Pathol. Pharmacal., 29, 549–559, 1980 e Proc. AACR-ASCO, 21, Abst. 1020, p. 254, 1980) evidenced potential antagonist properties on DXR cardiotoxicity, but no selective affect has been reported.

According to the present invention, anti-anthracycline MAbs are prepared as described in EP-A 03416776 and Int. J. Cancer 42, 798–802, 1988 and Anticancer Res. 10, 129–132, 1990, from the hybridoma deposited at ECACC under No. 90011003 on Jan. 12, 1990. Briefly, such hybridomas are obtained by fusing splenocytes of BALB/c mice subjected to an unrelated antigenic stimulus and treated for a short period of time with the specific antigen, as disclosed in U. S. Pat. No. 5,177,016. Monoclonal antibodies obtained according to such procedure are able to react with different epitopes of the anthracycline glycosides molecules. It has now been surprisingly found that these antibodies possess the property of modulating at a different degree the multifactorial type of interaction occurring between anthracycline drug molecules and cell populations. The point is of utmost relevance owing to the fact that in the case of administration of cytotoxic agents (such as anthracycline derivatives) the outcome of positive or negative biologic action, i.e. the onset of either therapeutic or toxic affects, depends on the characteristics of the interaction.

In operative conditions, advantage can be taken from this novel anti-anthracycline MAb property to improve the otherwise narrow therapeutic index of anthracycline drugs. Indeed, such monoclonal antibodies can be administered to animals, e.g. human patients, affected by tumors which are sensitive to treatment with anthracyclines, preferably before the anthracycline antibiotic treatment, or after, in case of extravasation lesions.

Thus, the invention includes a composition useful for cytostatic therapy comprising anthracycline antibiotic and an antidotal effective amount of an anti-anthracycline antibiotic monoclonal antibody produced from a hybridoma deposited at ECACC under No. 90011003 on Jan. 12, 1990. However, the invention also included composition useful for decreasing the toxic affect in animals caused by the administration of anthracycline antibiotics for cytostatic therapy wherein the composition comprises an antidotal effective amount of the anti-anthracycline antibiotic monoclonal antibody. Further, the invention includes a method of cytostatic therapy in animals, e.g. humans, comprising administering to an animal in need of such therapy an anthracycline antibiotic and an antidotal effective amount of the anti-anthracycline antibiotic monoclonal antibody. Finally, the invention includes a topical pharmaceutical composition useful for decreasing the toxic affect in animals caused by the administration of an anthracycline antibiotic comprising an antidotal effective amount of the anti-anthracycline antibiotic monoclonal antibody.

All of the foregoing are directed to decreasing the toxic affect of administration of the anthracycline antibiotic, and an effective amount of the monoclonal antibody can vary considerably. The detoxifying effect is generally proportional to the amount of the antibody administered, and, hence, even a very small amount will produce some detoxifying effect. Hence, the amount administered is not critical to the effect produced and is only related to the degree of the effect produced. However, generally speaking, the amount of the antibody administered for essentially maximum effectiveness will be substantially equimolar with the amount of anthracycline antibiotic administered, although this amount can be up to twice or more that amount. For certain administrations of the antibody, certain dosages are preferred, as set forth below.

DESCRIPTION OF PREFERRED EMBODIMENTS

In a preferred embodiment, the present invention provides a pharmaceutical composition comprising:
 a) an anthracycline drug, and
 b) a monoclonal antibody specific against anthracyclines,
  said compounds a) and b) may be formulated separately for prior, simultaneous, separate or sequential use in cytostatic therapy.

The formulation of the anthracycline drug can be carried out according to conventional techniques such as lyophilization of an active compound solution in vials, e.g. containing 5, 10 or 20 mg thereof, the 10 mg dosage having been found to be more suitable for use in clinical setting. The MAb preparation for human use should be purified by extended chromatographic procedures based on elution of the active fraction with salt solutions (such as elution buffer: 10 mM citric acid/sodium citrate at pH 5.5 or 3.5 depending on the IgG class). The eluate should eventually be submitted to dialysis through a semipermeable membrane and lyophilized in vials, e.g. containing 25 or 50 mg, of immunoglobulin together with a suitable caking component (such as mannitol).

A plain solution can be obtained by adding sterile water to the lyophilized preparation. Different formulations can be prepared by using, instead of water, balanced salt solutions such as saline buffered solution or Ringer salt solution or similar preparations.

The clinical administration of the present MAb is usually by i.v. route, immediately before the injection of anthracycline drug, and usually at equal weight ratio therewith.

The MAb dosage can be precautionally increased to 1.5–2 weight ratio in high risk patients such as the ones previously treated with subtoxic doses of cytotoxic drugs. In these patients, the MAb administration is of value in preventing the onset of the so-called "recall phenomena". These life endangering side affects are not rare when a new course of anthracycline treatment is given to pretreated subjects. The MAb dose can be diminished to 0.5 weight ratio in subjects submitted to short term treatment as it is carried out in an induction phase of leukemia chemotherapy.

The doses of MAb that can be usually reached in clinical practice vary from 50 to 75 mg/square meter of body surface. This dosage is comparable to that commonly used for MAb application in clinical setting. In this regard, it is noted that a year long clinical study has established 80 mg/square meter of body surface as a useful dosage of Doxorubicin, the most widely used anthracycline derivative.

Another embodiment of the invention provides a topical pharmaceutical composition containing the anti-anthracycline MAb, useful for treatment of extravasation. In the case of limited extravasation with scanty involvement of vein surrounding tissues (such as at the dorsum of the hand, a preferred site for this treatment), skin application of a preparation for topical use containing MAb, either as a solution or mixed with suitable excipients or entrapped in liposomes (as hereinafter described), may be used.

In the case of extravasation, either of major size or taking place at sites with substantial involvement of vein surround tissues, a MAb solution may be administered by local infiltration. A few general principals, as follows, should be observed for correct application of the MAb. Anthracycline molecules have the characteristics of being rapidly and strongly bound by biologic molecules present in perivenous tissues and slowly released so that an admittedly low, but still cytotoxic concentration of free drug can last in situ for a long period of time. In this case, it is advisable to administer at the site of extravasation low amounts of MAb, e.g. at a 1/10 ratio in comparison with the drug, provided that the administration is repeated until the last significant amount of drug (which is set free by intoxicated cell death) is sequestered by the MAb and detoxified. This procedure is recommended chiefly when the extravasated drug invades loose, areolar or adipose connective tissues. When the extravasation takes place in fibrous, aponeurotic tissue it can happen that a blister is formed, and in this case, an immediate local injection of MAb at high concentrations , e.g. at a 10 times ratio, should be carried out.

In still another embodiment, the invention provides a pharmaceutical preparation containing anti-anthracycline MAb entrapped in liposomes for topical administration for the prevention of alopecia. Briefly, the liposomes are prepared by mixing chloroform solutions of phosphatidylcholine, phosphatidylserine, cholesterol (75/15/10 weight ratio) or analogous formulations. The organic solvent is then removed by evaporation, and a MAb solution at a concentration of, for example, from 01. to 1 mg/ml is added to the dried lipid film. The preparation of multilamellar vesicles is made easier by vortex dispersion and further sonication.

The local application of the pharmaceutical preparation containing liposomes loaded with the anti-anthracycline MAb, applied one hour before the drug injection, exerts a definite protective effect on the hair roots, as shown by in vivo data. Briefly, 30 eight-day old Wistar rats were randomly allocated to three groups, namely: Group A (treated with topical application of MAb preparation); Group B (treated with topical application of liposomes, as a control group); and Group C (no treatment, as a control group). All the animals were dosed i.p. with an anthracycline derivative (Doxorubicin, 4 mg/Kg body weight) and the onset of alopecia areas were evaluated.

The results show that impairment of hair growth (by inhibition of the hair follicle function) and the onset of alopecia to be very low or absent in Group A, while they were clearly appreciable and very pronounced in control groups (B and C).

As far as the prevention of drug-induced alopecia is concerned, the MAb treatment can be especially useful for patients, mainly females, which, according to extended clinical observation, are liable to regard hair loss as a very distressing insult and a visible sign of the disease. In these cases, the administration of the MAb can contribute not only to diminishing the drug toxicity, but also to increase the quality of life of the patients by preventing the onset of depression syndromes.

In vitro and in vivo experiments are described hereinbelow to illustrate the antidotal affects of anti-anthracycline MAbs.

Even though the invention is illustrated specifically referring to DXR, analogue results are obtained using other antibody/antibiotic couples, which obviously are included within the spirit and scope of the invention itself.

BALB/c, DBA/2. C57BL/6 x DBA/2 (BD2-F1) mice were used in the reported examples.

Ascitic fluid produced by mice injected with the anti-DXR hybridomas or unrelated hybridomas secreting MAbs directed against different antigens (human ovarian carcinoma) was used for in vivo tests. For in vitro tests, anti-DXR MAbs were purified by affinity chromatography on a Protein-A-Sepharose column (Pharmacia).

P388 leukemia cells and mice splenocytes were cultured according to conventional methods.

The in vivo test is that of DXR cytotoxic effect on normal mouse splenocytes.

EXAMPLE 1

In Vivo Experiments

The usual toxic effect of DXR in BALB/c mice treated DXR was almost completely inhibited by administration of the anti-DXR MAb. Particularly, the usual marked decrease of body weight consistently associated with i.p. administration of 16 mg/kg of DXR (a toxic dose of BALB/c mice) was consistently reversed in animals also treated with a corresponding dose of MAb.

Moreover, whereas in DXR toxicity, a period of at least 3 months from the end of the treatment is necessary for the animals to reach the initial body weight, the growth curve of the mice treated with DXR and simultaneously with the anti-DXR MAb was almost equivalent to that-of an untreated control group. Even the affect of higher doses of DXR was almost completely inhibited by MAb administration, as ascertained on the basis of mortality curves of BALB/c mice.

Further, the mean toxic dose $TD_{50}$ of DXR in the presence of the MAb was much higher than in its absence.

EXAMPLE 2

In Vivo and In Vitro Experiments

This test shows that the antidotal effect exerted by the MAb on the toxic effect of DXR does not result in a decrease of the drug's therapeutic efficacy.

Tests were carried out on hybrid BD2-F1 mice injected with P388 leukemia cells and different doses of DXR, either alone (as part of a control group) or with anti-DXR MAb (the test group) or with an unrelated MAb (another part of the control group).

The mean survival time of animals receiving anti-DXR MAb (the test group) was substantially greater and the number of long-term survivors was substantially greater than the control.

Control tests showed that the anti-DXR MAb is Der se devoid of a direct activity on the growth of P388 leukemia cells, either in vitro or in vivo.

What is claimed is:

1. A topical pharmaceutical composition useful in cytostatic therapy comprising an anthracycline antibiotic and an antidotal effective amount of an anti-anthracycline antibiotic monoclonal antibody produced from hybridoma deposited at ECACC under No. 90011003 on Jan. 12, 1990 and a pharmaceutically acceptable topical carrier.

2. The composition of claim 1 wherein the anthracycline antibiotic is doxorubicin.

3. The composition of claim 1 wherein the amount of the monoclonal antibody is sufficient that toxic affects of the anthracycline antibiotic on normal tissue is less than that on tumor cells.

4. A topical pharmaceutical composition useful for decreasing the toxic affect in animals caused by the administration of an anthracycline antibiotic for cytostatic therapy comprising an antidotal effective amount of an anti-anthracycline antibiotic monoclonal antibody produced by a hybridoma deposited at ECACC under No. 90011003 on Jan. 12, 1990, and a pharmaceutically acceptable topical carrier.

5. The composition of claim 4 wherein the carrier is a solvent, excipient or liposome.

6. The composition of claim 4 wherein the carrier is suitable for topical application to extravasation lesions.

7. The composition of claim 4 wherein the carrier is a solvent for the monoclonal antibodies.

8. The composition of claim 7 wherein the solvent is suitable for local infiltration.

9. The composition of claim 4 wherein the carrier is an excipient for the monoclonal antibodies.

10. The composition of claim 4 wherein the carrier is suitable for application in preventing anthracycline-induced alopecia.

11. A method of cytostatic therapy in animals, comprising topically administering to an animal in need of such therapy an anthracycline antibiotic and an antidotal effective amount of an anti-anthracycline antibiotic monoclonal antibody produced from a hybridoma deposited at ECACC under No. 90011003 on Jan. 12, 1990 in a pharmaceutically acceptable topical carrier.

12. The method of claim 11 wherein the monoclonal antibody is administered before, during or after administration of the anthracycline antibiotic.

13. The method of claim 12 wherein the monoclonal antibody in the carrier is applied directly to extravasation lesions produced by administration of the anthracycline antibiotic.

14. The method of claim 13 wherein the monoclonal antibody is carried in a solvent therefor.

15. The method of claim 11 wherein the monoclonal antibody is topically applied as a preventative for anthracycline-induced alopecia.

* * * * *